(12) United States Patent
Farha et al.

(10) Patent No.: US 8,322,534 B2
(45) Date of Patent: Dec. 4, 2012

(54) PURIFICATION OF METAL-ORGANIC FRAMEWORK MATERIALS

(75) Inventors: Omar K. Farha, Morton Grove, IL (US); Joseph T. Hupp, Northfield, IL (US)

(73) Assignee: Northwestern University, Evanston, IL (US)

( * ) Notice: Subject to any disclaimer, the term of this patent is extended or adjusted under 35 U.S.C. 154(b) by 331 days.

(21) Appl. No.: 12/661,771

(22) Filed: Mar. 23, 2010

(65) Prior Publication Data

US 2010/0267951 A1 Oct. 21, 2010

Related U.S. Application Data

(60) Provisional application No. 61/210,980, filed on Mar. 25, 2009.

(51) Int. Cl.
*B03D 1/00* (2006.01)
(52) U.S. Cl. .................................................. 209/172
(58) Field of Classification Search ................ 209/162, 209/163, 172, 172.5, 173
See application file for complete search history.

(56) References Cited

U.S. PATENT DOCUMENTS

| | | | | |
|---|---|---|---|---|
| 4,510,254 A | * | 4/1985 | Morris et al. | 501/146 |
| 4,591,431 A | * | 5/1986 | Sinha | 209/3 |
| 6,930,193 B2 | | 8/2005 | Yaghi et al. | 556/46 |
| 2004/0050805 A1 | * | 3/2004 | Hartleitner et al. | 210/800 |
| 2006/0115420 A1 | * | 6/2006 | Fellers | 423/700 |

OTHER PUBLICATIONS

Farha et al. "Separating Solids: Purification fo Metal-Organic Framework Materials", J. Am. Chem. Soc., Jun. 2008, 130 (27), 8598-8599.*

D. Bradshaw, et al, Design, Chirality, and Flexiblity in Nanoporous Molecule-Based Materials, Acc. Chem. Res., (2005), 38, pp. 273-282.

R. Snurr, et al., Prospects for Nanoporous Metal-Organic Materials in Advanced Separations Processes, AIChE Journal, (2004), 50, pp. 1090-1095.

S. Kitagawa, et al., Functional Porous Coordination Polymers, Angew. Chem. Int. Ed., (2004), 43, pp. 2334-2375.

R. Kitaura, et al., Immobilization of a Metallo Schiff Base into a Microporous Coordination Polymer, Angew. Chem. Int. Ed., (2004), 43, pp. 2684-2687.

B. Chen, et al., High $H_2$ Adsorption in a Microporous Metal-Organic Framework with Open Metal Sites, Angew. Chem. Int. Ed., (2005), 44, pp. 4745-4749.

M. Latroche, et al., Hydrogen Storage in the Giant-Pore Metal-Organic Frameworks MIL-100 and MIL-101, Angew. Chem. Int. Ed., (2006), 45, pp. 8227-8231.

S.-H. Cho, et al., A metal-organic framework material that functions as an enantioselective catalyst for olefin epoxidation, Chem. Commun., (2006), pp. 2563-2565.

S. James, Metal-organic Frameworks, Chem. Soc. Rev., (2003), 32, pp. 276-288.

B. Gómez-Lor, et al., Novel 2D and 3D Indium Metal-Organic Frameworks: Topology and Catalytic Properties, Chem. Mater., (2005), 17, pp. 2568-2573.

B.-Q. Ma, et al., Microporous Pillard Paddle-Wheel Framework Based on Mixed-Ligand Coordination of Zinc Ions, Inorg. Chem., (2005), 44, pp. 4912-4914.

(Continued)

*Primary Examiner* — Frank Lawrence, Jr.

(57) ABSTRACT

A method of purification of a solid mixture of a metal-organic framework (MOF) material and an unwanted second material by disposing the solid mixture in a liquid separation medium having a density that lies between those of the wanted MOF material and the unwanted material, whereby the solid mixture separates by density differences into a fraction of wanted MOF material and another fraction of unwanted material.

6 Claims, 3 Drawing Sheets

OTHER PUBLICATIONS

D. Collins, et al., Hydrogen storage in metal-organic frameworks, J. Mater. Chem., (2007), 17, pp. 3154-3160.

E. Lee, et al., Multifunctionality and Crystal Dynamics of a Highly Stable, Porous Metal-Organic Framework [$Zn_4O(NTB)_2$], J. Am. Chem. Soc., (2005), 127, pp. 6374-6381.

C.-D. Wu, et al., A Homochiral Porous Metal-Organic Framework for Highly Enantioselective Heterogeneous Asymmetric Catalysis, J. Am. Chem. Soc., (2005), 127, pp. 8940-8941.

M. Dincă, et al., Strong $H_2$ Binding and Selective Gas Adsorption within the Microporous Coordination Solid $Mg_3(O_2C—C_{10}H_6—CO_2)_3$, J. Am. Chem. Soc., (2005), 127, pp. 9376-9377.

D. Sun, et al., An Interweaving MOF with High Hydrogen Uptake, J. Am. Chem. Soc., (2006), 128, pp. 3896-3897.

M. Dincă, et al., Hydrogen Storage in a Microporous Metal-Organic Framework with Exposed $Mn^{2+}$ Coordination Sites, J. Am. Chem. Soc., (2006), 128, pp. 16876-16883.

J. Hafizovic, et al., The Inconsistency in Adsorption Properties and Powder XRD Data of MOF-5 Rationalized by Framework Interpenetration and the Presence of Organic and Inorganic Species in the Nanocavities, J. Am. Chem. Soc., (2007), 129, pp. 3612-3620.

K. Mulfort, et al., Chemical Reduction of Metal-Organic Framework Materials as a Method to Enhance Gas Uptake and Binding, J. Am. Chem. Soc., (2007), 129, pp. 9604-9605.

O. Farha, et al., Synthesis and Hydrogen Sorption Properties of Carborane Based Metal-Organic Framework Materials, J. Am. Chem. Soc., (2007), 129, pp. 12680-12681.

S. Ma, et al., Framework-Catenation Isomerism in Metal-Organic Frameworks and Its Impact on Hydrogen Uptake, J. Am. Chem. Soc., (2007), 129, pp. 1858-1859.

F. Nouar, et al., Supermolecular Building Blocks (SBBs) for the Design and Synthesis of Highly Porous Metal-Organic Frameworks, J. Am. Chem. Soc., (2008), 130, pp. 1833-1835.

J. Rowsell, et al., Metal-organic frameworks: a new class of porous materials, Microporous and Mesoporous Materials, (2004), 73, pp. 3-14.

A. Sudik, et al., Design, Synthesis, Structure, and Gas ($N_2$, Ar, $CO_2$, $CH_4$, and $H_2$) Sorption Properties and Porous Metal-Organic Tetrahedral and Heterocuboidal Polyhedra, J. Am. Chem. Soc., (2005), 127, pp. 7110-7118.

M. Eddaoudi, et al., Systematic Design of Pore Size and Functionality in Isoreticular MOFs and Their Application in Methane Storage, Science, (2002), 295, pp. 469-472.

\* cited by examiner

PURIFICATION OF METAL-ORGANIC FRAMEWORK MATERIALS

This application claims benefits and priority of U.S. provisional application Ser. No. 61/210,980 filed Mar. 25, 2009, the disclosure of which is incorporated herein by reference.

CONTRACTUAL ORIGIN OF THE INVENTION

This invention was made with government support under Grant No. DE-FG02-01ER15244 awarded by the Department of Energy and under Grant No. EEC-0647560 awarded by the National Science Foundation. The Government has certain rights in the invention.

FIELD OF THE INVENTION

The present invention relates to a method of purification of a crude (contaminated) metal-organic framework material that includes another unwanted material, which may be another metal-organic framework material or other unwanted material.

BACKGROUND OF THE INVENTION

A tremendous development in the area of functional, nanostructured materials is the emergence of large numbers of structurally well defined, permanently microporous metal-organic framework materials (MOFs). Consisting of metal-ion or -cluster nodes and multi-topic organic struts, such materials are often characterized by very large internal surface areas, low densities, and uniformly sized channels and pores.[1] Among the many applications that may capitalize on these extraordinary properties are gas storage,[2] chemical separations,[3] and selective catalysis[4].

MOFs are generally synthesized via one-pot solvothermal methods. Since purification of the resulting network solids is not feasible via the methods usually employed by chemists (distillation, recrystallization, chromatography, sublimation, etc.), a premium is placed on discovering conditions that yield pure products. Typically, discovery entails systematically evaluating scores of reaction conditions that differ only slightly from initial or refined conditions (e.g. temperature, solvent composition, reactant concentrations, reaction time, and even reaction vessel size). Alternatively, if sufficiently large crystals of distinct morphology or color are obtained, they can be manually separated from undesired byproducts—albeit, often in painstaking fashion. Nevertheless, isolation of pure MOF materials is essential; closely structurally related porous materials can often differ enormously in terms of properties and functional behavior.[5] Density separation has occasionally been used to isolate molecular metal complexes, but it is not well developed for metal-organic framework chemistry.[6] References 1-6 are set forth below in the Reference list.

SUMMARY OF THE INVENTION

The present invention relates to a method of purification of a solid mixture of a metal-organic framework material and an unwanted second material, which may be another metal-organic framework material. The present invention envisions disposing a solid mixture containing a wanted or desired MOF material to be isolated and an unwanted material in a liquid separation medium, such as an organic solvent, having a density that lies between those of the wanted MOF material and the unwanted material, whereby the solid mixture separates by density differences into a fraction of wanted MOF material and a fraction of unwanted material.

The present invention also envisions disposing a solid mixture containing a wanted MOF material to be isolated and an unwanted second material in a first liquid separation medium, such as a first organic solvent, having a density greater than that of the wanted MOF material and introducing a second liquid separation medium, such as a second organic solvent miscible in the first separation liquid, having a lesser density in a manner to adjust the collective density of the separation liquid so that it lies between those of the wanted MOF material and the unwanted material, whereby the solid mixture separates into a floating fraction of the wanted MOF material and a sinking fraction of the unwanted material.

The present invention is advantageous for rapidly purifying an MOF material and its applicability for use for three problems commonly encountered in purifying an MOF material: 1) isolation of a desired crystalline MOF material from a solid mixture containing a second compound comprising the same organic-strut and/or metal-ion building blocks, 2) separation of a desired mixed-organic strut material from a second crystalline MOF material containing only a single type of organic strut, and 3) separation of a non-interpenetrating MOF material from an otherwise identical material consisting of catenated networks. The method is not limited to these uses and may be practiced to purify MOF materials vis-à-vis other materials including, but not limited to, linear coordination polymers or insoluble metal salts.

Other advantages of the present invention will become apparent from the following detailed description taken with the following drawings.

DETAILED DESCRIPTION OF THE INVENTION

Figure 1:
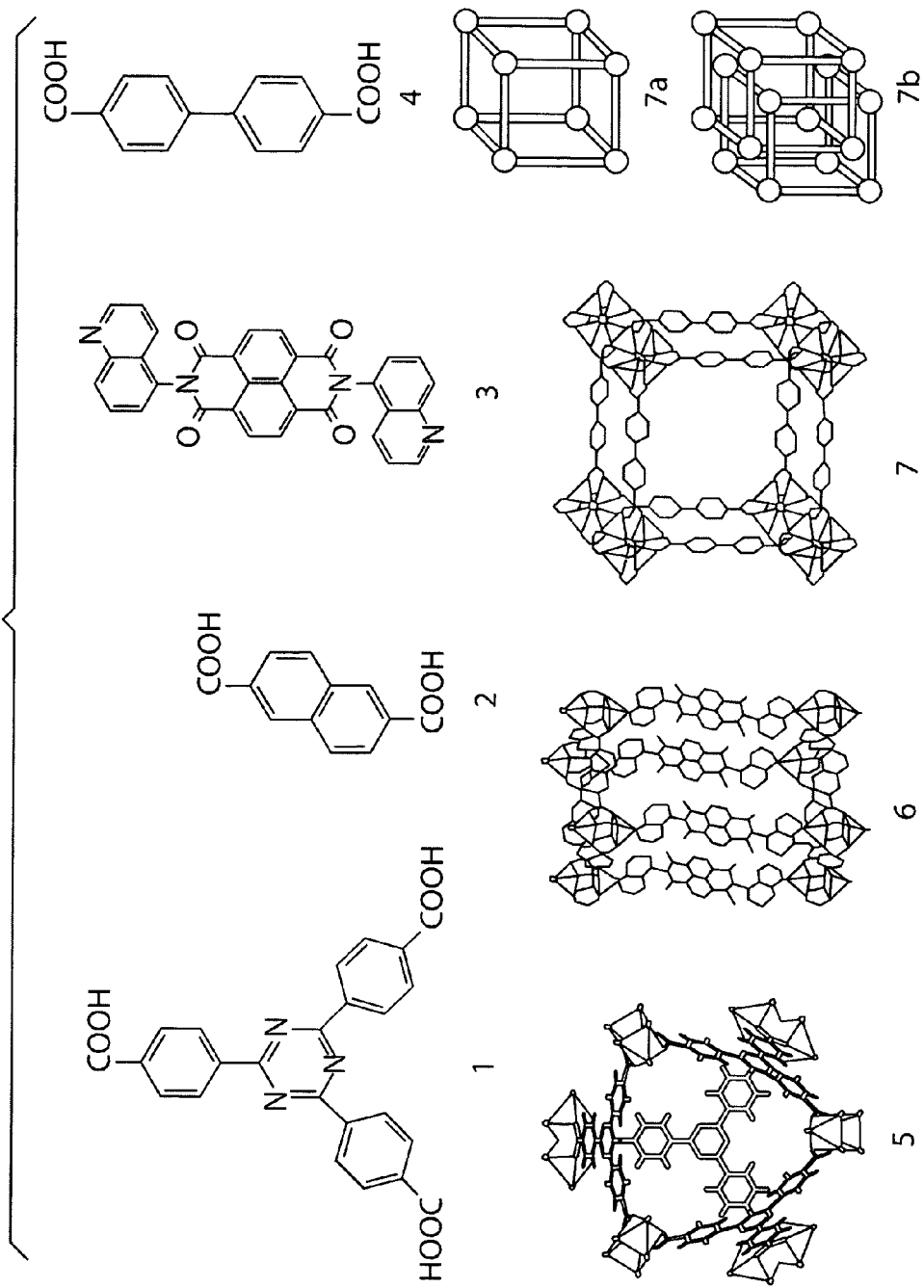
FIG. 1 includes representations of structures of organic struts and MOFs. 1: 4,4',4"-s-triazine-2,4,6-triyltribenzoate (TATB); 2: 1,4-naphthalenedicarboxylate (NDC); 3: N,N'-di-(5-aminoquinoline)-1,4,5,8-naphthalenetetracarboxydiimide (diQuNI); 4: 4,4'-biphenyldicarboxylic acid (BPDC). 5-7: are described below in specification. Zn(II) ions shown as tetrahedra functioning as metal-ion building blocks. For clarity, interwoven networks are omitted.

The present invention relates to a method of purification of a solid mixture of a metal-organic framework (MOF) material and an unwanted second material, which may be another metal-organic framework material with a different framework structure and/or morphology. An illustrative embodiment of the invention involves disposing the solid mixture containing the wanted MOF material to be isolated and the unwanted material in a liquid separation medium, such as an organic solvent, having a density that lies between those of the wanted MOF material and the unwanted material, whereby the solid mixture separates by density differences into a fraction of wanted MOF material and a fraction of unwanted material. The method is both straightforward and broadly applicable. The method of the present invention can be used to isolate even minor components (e.g. 15%) of mixed solid materials (phases, compounds, and the like).

In another illustrative embodiment, the present invention envisions disposing a solid mixture in a first separation liquid, such as an organic solvent, having a density greater than that of the wanted MOF material so that it will float on the first liquid separation medium and then and introducing a second liquid separation medium, such as another organic solvent miscible in the first separation liquid, having a density less than that of the first liquid separation medium in a manner to adjust the collective density of the collective liquid separation medium (the separation medium having the first and second miscible separation liquids) so that it lies between those of the wanted MOF material and the unwanted material, whereby the solid mixture separates into a floating fraction of wanted MOF material and a sinking fraction of unwanted material.

The present invention can be practiced to purify a crude (contaminated) solid mixture that, as synthesized, contains a wanted MOF to be isolated and an unwanted second material, which may be another metal-organic framework material or other contaminate material. For example, the present invention envisions purifying the crude solid mixture in a manner to 1) isolate a desired crystalline MOF from a mixture containing a second compound comprising the same organic-strut and/or metal-ion building blocks (e.g. Zn(II) ions as tetrahedra), 2) separate a desired mixed-organic strut material from a second crystalline MOF containing only a single type of organic strut, and 3) separate a non-interpenetrating MOF from an otherwise identical material consisting of catenated networks. The method is not limited to these uses and may be practiced to purify MOF materials vis-à-vis other materials including, but not limited to, linear coordination polymers or insoluble metal salts.

In an illustrative embodiment of the invention, $CH_2BrCl$ can be used as the first or parent solvent (first separation liquid) because of its high density (1.99 g/cm$^3$) relative to most MOFs. Starting with a dense first or parent solvent allows the synthesized crude MOF mixture to float. Subsequently, a second miscible but lighter solvent is added until the appropriate density is reached and the solid mixture separates into floating and sinking fractions. Powder x-ray diffraction (PXRD) data can then be obtained for both fractions and afterward compared to candidate simulated PXRD patterns. This procedure should be completed quickly, i.e. before significant solvent exchange with the porous MOF takes place. Once a solvent of appropriate density is obtained, MOF material separation typically occurs within a few tens of seconds or less.

The following Examples are offered to further illustrate but not limit the invention:

Example 1

Figure 2A:
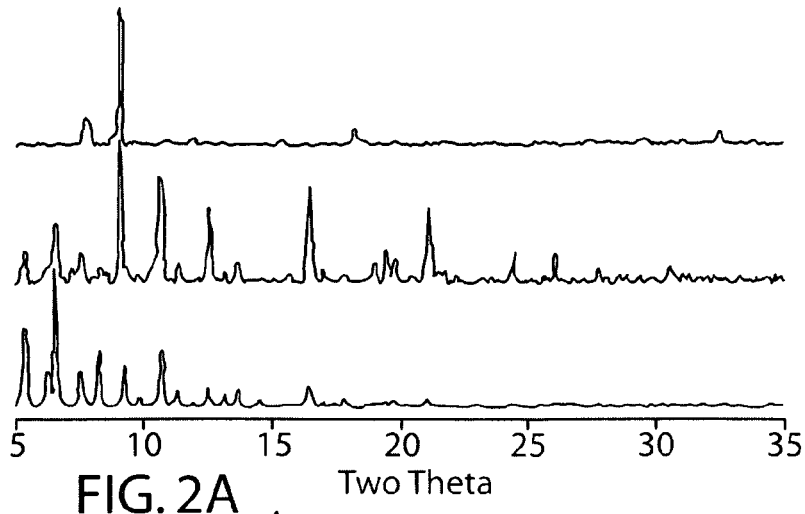
FIG. 2A is a powder x-ray diffraction for example 1. Structure 5 simulation (bottom plot), 5 after separation (middle plot), and green needle impurities (top plot).
Figure 2B:
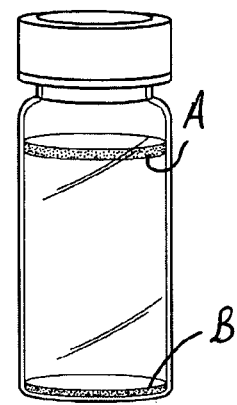
FIG. 2B represents a vial after separation was achieved with teal-colored crystals of MOF material (A) as a separate top separate floating layer and green needle impurities (B) as a bottom separate sinking layer.

The two-fold interpenetrated MOF, $Cu_3(TATB)_2(H_2O)_3$ (5), was obtained by reacting $Cu(NO_3)_2·3H_2O$ with 1 in DMSO at 120° C. as described by Sun et al[7], the teachings of which are incorporated herein by reference While capable of yielding pure 5 (diamond shaped teal crystals), the method also sometimes produced a mixture of 5 and a second phase consisting of crystalline green needles that analyzed for twice the Cu content of 5. For example, twenty nominally identical reactions were run. Three samples yielded the desired MOF in pure form, five samples yielded brown amorphous material, and the twelve samples produced a combination of the two crystalline materials in a range of ratios. The solid mixture of crystalline compounds was purified by: a) sonicating, b) filtering, c) washing with DMSO, and d) depositing the solid mixture in a conventional separation funnel, followed by addition of 1:5 (v:v) $DMSO:CH_2BrCl$ (liquid separation medium) pursuant to the invention whose density is between those of the teal crystals and the green needles. Within seconds of the addition the teal crystals (A in FIG. 2B) floated to the liquid surface and the green needles (B in FIG. 2B) sank. The needles were removed and the procedure was repeated to ensure the purity of the desired top layer. The purified teal crystals were then collected. A single crystal X-ray structure as well as the PXRD pattern of the bulk sample (FIG. 2A) confirmed that the desired pure product (5) had been isolated. Powder X-ray diffraction (PXRD) patterns were recorded with a Rigaku XDS 2000 diffractometer using nickel-filtered Cu Kα radiation (λ=1.5418 Å). Single crystals were mounted on a BRUKER APEX2 V2.1-0 diffractometer. $^1H$ NMR and $^{13}C$ NMR measurements were done on a Varian Inova 500 spectrometer at 500 MHz and 125 Mhz, respectively. Elemental analyses were conducted by Atlantic Microlabs of Norcross, Ga.

The particular 1:5 (v:v) $DMSO:CH_2BrCl$ (liquid separation medium) used was initially determined pursuant to another embodiment of the invention by placing an amount of the synthesized solid mixture comprised of MOF material (5) and the second phase of crystalline green needles in a first or parent liquid separation medium comprised of pure $CH_2BrCl$. Then, DMSO (as the second liquid separation medium of lower density than the $CH_2BrCl$ liquid) was added incrementally until separation of the desired pure MOF product (5) from the second phase of crystalline green needles occurs as a result of density differences therebtween. The density of the collective separation liquid (i.e. the 1:5 (v:v) $DMSO:CH_2BrCl$ separation medium) thereby was adjusted to lie between those of the wanted pure MOF product (5) and the second phase of crystalline green needles to achieve separation and purification of the pure MOF product (5). The $CH_2BrCl$ was used as the first or parent starting solvent for this example (and the other examples set forth) below because of its high density (1.99 g/cm$^3$) relative to most MOFs.

For verification, the densities of material 5 and its impurity were determined via pycnometry and found to be 1.28 and 1.94 g/cm$^3$, respectively. The density of the solvent mixture was 1.82 g/cm$^3$.

Example 2

Figure 3:
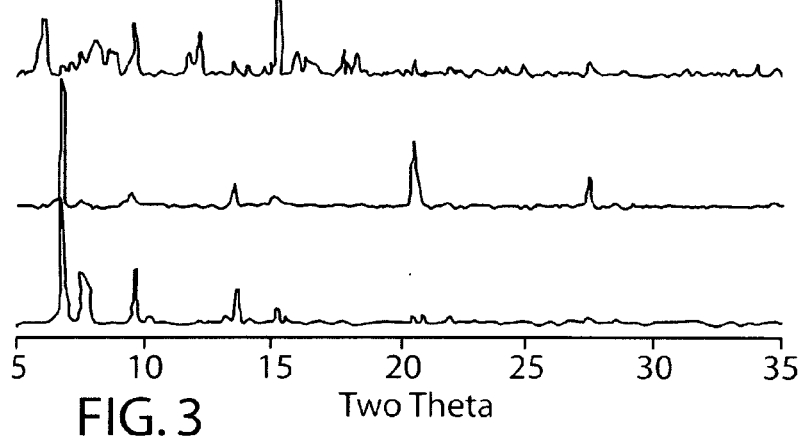
FIG. 3 is a powder x-ray diffraction for example 2. Structure 6 simulation (bottom plot), 6 after purification (middle plot) and white impurities (top plot).

A new doubly-interwoven, pillared-paddlewheel[8] MOF, $Zn_2(NDC)_2(diQuNI)$ (6, yellow crystals), was synthesized by reacting 2 (FIG. 1), 3 (FIG. 1), and $Zn(NO_3)_2·6H_2O$ in diethylformamide (DEF) as described below. The crude product, however, was contaminated with a white crystalline material. MOF 6 was purified similarly to MOF 5 in Example 1, but with a liquid separation medium of 2:5 (v:v) $DMF:CH_2BrCl$. The desired mixed-ligand compound floated while the contaminant sank. PXRD plots for both fractions are shown in FIG. 3.

The particular 2:5 (v:v) DMF:CH$_2$BrCl (liquid separation medium) used was initially determined pursuant to the invention using the method like that described in Example 1 with the difference being that DMF was added to the pure CH$_2$BrCl, instead of DMSO, until separation of the MOF 6 and contaminant occurred.

The structure of MOF 6 was established by single-crystal X-ray measurements. $^1$H NMR of an acid-dissolved sample of the contaminant established that it contained NDC but not diQuNI; PXRD data are consistent with formation of an NDC-based cubic MOF or MOFs.[9]

For example, X-ray quality single crystals of MOF 6 were obtained upon heating Zn(NO$_3$)$_2$.6H$_2$O (15 mg, 0.05 mmol), H$_2$NDC (10 mg, 0.05 mmol) and diQuNI (6 mg, 0.01 mmol) in 5 ml DEF at 80° C. for 48 hours. Bright yellow crystals were picked from the crude mixture with white crystalline powder for single crystal analysis. Single crystal X-ray diffraction: Single crystals were mounted on a BRUKER APEX2 V2.1-0 diffractometer equipped with a graphite-monochromated MoK$\alpha$ ($\lambda$=0.71073 Å) radiation source in a cold nitrogen stream. All crystallographic data were corrected for Lorentz and polarization effects (SAINT). The structures were solved by direct methods and refined by the full-matrix least-squares method on F$^2$ with appropriate software implemented in the SHELXTL program package. All the non-hydrogen atoms were refined anisotropically. Hydrogen atoms were added at their geometrically ideal positions. Most of the DMF solvent molecules are severely disordered, which hindered satisfactory development of the model; therefore, the SQUEEZE routine (PLATON) was applied to remove the contributions of electron density from disordered solvent molecules. The outputs from the SQUEEZE calculations are attached to the CIF file. After purification, isolated yield: 8 mg (30% yield based on Zn). Anal. calcd. for 6.5H$_2$O, C$_{56}$H$_{33}$N$_4$O$_{14.5}$Zn$_2$: C, 59.80; H, 2.96; N, 4.98. Found: C, 59.41; H, 2.88; N, 5.28.

Synthesis of 3 (diQuNI): 1,4,5,8-naphthalenetetracarboxydianhydride (400 mg, 1.49 mmol), 5-aminoquinoline (472 mg, 3.27 mmol), and 40 ml pyridine were combined in a 100 ml 2-neck round bottom flask and heated to reflux overnight. After cooling, the solid was isolated by filtration and washed with acetone and hexanes and allowed to dry in air. Isolated yield: 279 mg, 36%. $^1$N NMR (TFA-d): δ 9.16 (d, J=5.0 Hz, 2H), 9.04 (d, J=9.0 Hz, 2H), 8.98 (s, 4H), 8.49 (d, J=9.0 Hz, 2H), 8.35 (t, J=9.0 Hz, 2H), 8.12 (d, J=8.0 Hz, 2H), 8.07 (t, J=8.0 Hz, 2H). MALDI-TOF MS: obs 521.98; calcd [M+H]$^+$521.49. Anal. calcd. for 3, C$_{32}$H$_{16}$N$_4$O$_4$: C, 73.84; H, 3.10; N, 10.76. Found: C, 72.98; H, 3.34; N, 11.10.

Example 3

Figure 4A:
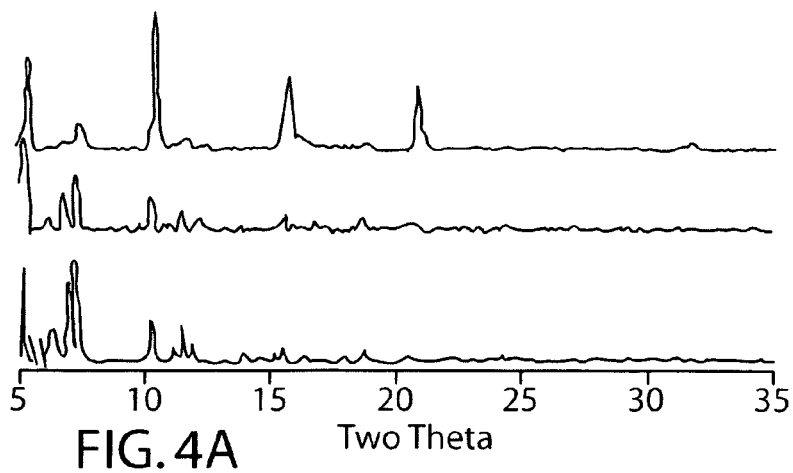
FIG. 4A is a powder x-ray diffraction for example 3. 7a simulation (bottom plot), 7a after purification (middle plot) and 7b (top plot). Material 7 is 7a. The asterisk * indicates that the peak intensity is reduced by 80% in order to elucidate the rest of the spectrum.
Figure 4B:
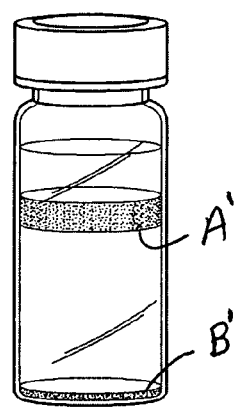
FIG. 4B represents a vial after separation was achieved with IRMOF-10 (A') floating as a separate upper layer while IRMOF-9 (B') sinking as a separate layer.

IRMOF-10 (7a, non-catenated structure)[9] was synthesized utilizing 4, essentially as described by Yaghi et al.[9], the teachings of which are incorporated herein by reference, except that DMF replaced DEF as solvent (IRMOF means isoreticulare MOF). As is often the case in MOF syntheses, this seemingly minor change had significant consequences: 7a was contaminated with substantial amounts of IRMOF-9 (7b), the two-fold interwoven analogue of 7a. The mixture was separated by using a 4:5:26 (v:v:v) solution (liquid separation medium) of CH$_2$Cl$_2$:CHCl$_3$:CH$_2$BrCl. In this solution, IRMOF-10 (A' in FIG. 4B) floated as a separate layer while IRMOF-9 (B' in FIG. 4B) sank as a separate layer. A single-crystal X-ray structure for 7a has not been reported. The PXRD of the sample is shown in FIG. 4A. Finally, independently synthesized, pure samples of 7a and 7b were intentionally combined and then successfully density-separated.

The particular 4:5:26 (v:v:v) solution (liquid separation medium) of CH$_2$Cl$_2$:CHCl$_3$:CH$_2$BrCl used was initially determined pursuant to the invention using the method like that described in Example 1 with the difference being that CH$_2$Cl$_2$ and CHCl$_3$ were added to the pure CH$_2$BrCl CH$_2$ClBr:CH$_3$Cl, instead of DMSO, until separation of the mixture occurred.

Example 4

Figure 5:
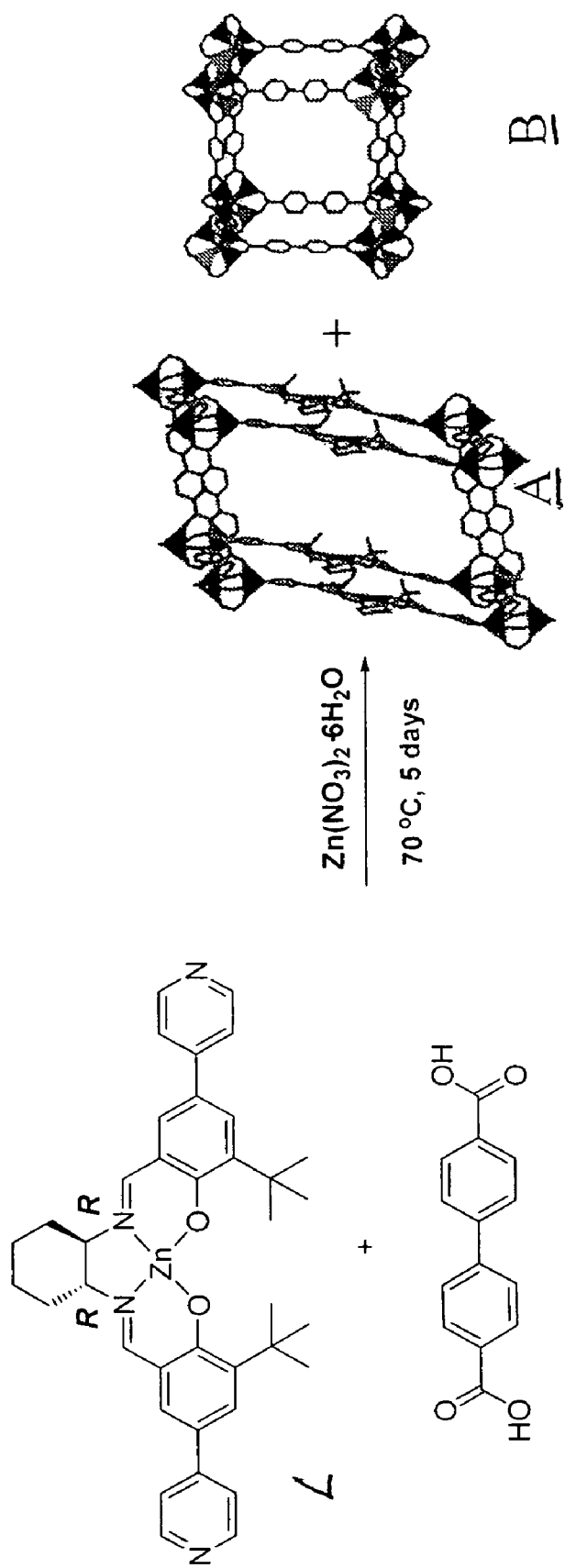
FIG. 5 is a diagrammatic view of $H_2bpdc$ and L reacted with $Zn(NO_3)_2$ of Example 4 to synthesize a catalytically active MOF material (A) and a non-reactive MOF species (B).

A Zn$_2$(bpdc)$_2$(L).10DMF.8H$_2$O MOF material was prepared in a vial by introducing Zn(NO$_3$)$_2$ 6H$_2$O (12 mg, 0.04 mmol), H$_2$bpdc (7.2 mg, 0.03 mmol) and L (34 mg, 0.05 mmol) with DMF, 6 mL) (see FIG. 5) as described in Cho et al., "A metal-organic framework material that functions as an enantioselective catalyst for olefin epoxidation", Chemical Communications, (Cambridge, United Kingdom) (2006), 24, 2563-265, the teachings of which are incorporated herein by reference, with the exception that Zn-salen was used instead of Mn-salen. The vial was capped and heated to 80° C. in an oil bath for one week, over which time brown blocked shape crystals slowly formed.

The cubic non-active MOF impurities were separated from the catalytically active MOF by suspending the solid mixture in 4:2:4 (v:v:v) solution (liquid separation medium) of CH$_2$ClBr:CH$_3$Cl:DMF in a separation flask pursuant to the invention, whereby the catalytically active MOF floated to the top and the inactive MOF impurities sank to the bottom of the separation flask.

The particular 4:2:4 (v:v:v) solution (liquid separation medium) of CH$_2$ClBr:CH$_3$Cl:DMF used was initially determined pursuant to the invention using the method like that described in Example 1 with the difference being that CH$_2$ClBr and CH$_3$Cl were added to the pure DMF until separation of the mixture occurred.

Example 5

Two MOF materials were synthesized from 1,12-dihydroxycarbonyl-1,12-dicarba-closo-dodecaborane (1) (p-CDCH$_2$). Compound 1 and cobalt II salts were used to synthesize two new coordination polymer materials by varying the reaction solvent and temperature conditions as described by O. K. Farha et al., J. Am. Chem. Soc. 2007, 129, 12680, the teachings of which are incorporated herein by reference. A solid mixture of crystalline first MOF and crystalline second MOF with the different morphologies (block-like versus microcrystalline rods, respectively) were isolated from one another by placing a solid mixture thereof in chloroform whose density is between those of the first and second MOF's, whereby the first MOF floated to the top and the second MOF sank to the bottom of the separation flask.

Although the present invention has been described with respect to certain embodiments, those skilled in the art will appreciate that changes and modifications can be made thereto within the scope of the invention as set forth in the appended claims.

References which are incorporated herein by reference:
1. Recent reviews: (a) Collins, D. J.; Zhou, H-C. *J. Mat. Chem.* 2007, 17, 3154-3160. (b) Rowsell, J. L. C.; Yaghi, O. M. *Micro. and Meso. Mat.* 2004, 73, 3-14. (c) James, S. L. *Chem. Soc. Rev.* 2003, 32, 276-288.
2. See, for example: (a) Nouar, F.; Eubank, J. F.; Bousquet, T.; Wojtas, L.; Zaworotko, M. J.; Eddaoudi, M. *J. Am. Chem. Soc.* 2008, 130, 1833-1835. (b) Chen, B.; Ockwig, N. W.; Millard, A. R.; Contreras, D. S.; Yaghi, O. M. *Angew. Chem. Int. Ed.* 2005, 44, 4745-4749. (c) Dinca, M.; Dailly, A.; Liu, Y.; Brown, C. M.; Neumann, D. A.; Long, J. R. *J. Am. Chem. Soc.* 2006, 128, 16876-16883. (d) Bradshaw, D.; Claridge, J. B.; Cussen, E. J.; Prior, T. J.; Rosseinsky, M. J. *Acc. Chem. Res.* 2005, 38, 273-282. (e) Kitagawa, S.; Kitaura, R.; Noro S. *Angew. Chem., Int. Ed.* 2004, 43, 2334-2375. (f) Latroche, M.; Surblé, S.; Serre, C.; Mellot-Draznieks, C.; Llewellyn, P. L.; Lee, H.; Chang, J.; Jhung, S. H.; Férey, G. *Angew. Chem., Int. Ed.* 2006, 45, 8227-8231. (g) Mulfort, K. L.; Hupp, J. T. *J. Am. Chem. Soc.* 2007, 129, 9604-9605. (h) Farha, O. K.; Spokoyny, A. M.; Mulfort, K. L.; Hawthorne, M. F.; Mirkin, C. A.; Hupp, J. T. *J. Am. Chem. Soc.* 2007, 129, 12680.
3. See, for example: (a) Lee, E. Y.; Jang, S. Y.; Suh, M. P. *J. Am. Chem. Soc.* 2005, 127, 6374-6381. (b) Dinca, M.; Long, J. R. *J. Am. Chem. Soc.* 2005, 127, 9376-9377. (c) Snurr, R. Q.; Hupp, J. T.; Nguyen, S. T. *AIChE,* 2004, 50, 1090-1095.
4. See, for example: (a) Cho, S.-H.; Ma, B.-Q.; Nguyen, S. T.; Hupp, J. T.; Albrecht-Schmitt, T. E. *Chem. Commun.* 2006, 2563-2565. (b) Wu, C. D.; Hu, A.; Zhang, L.; Lin, W. *J. Am. Chem. Soc.* 2005, 127, 8940-8941. (c) Gomez-Lor, B.; Gutierrez-Puebla, E.; Iglesias, M.; Monge, M. A.; Ruiz-Valero, C.; Snejko, N. *Chem. Mater.* 2005, 17, 2568-2573. (d) Kitaura, R.; Onoyama, G.; Sakamoto, H.; Matsuda, R.; Noro, S. I.; Kitagawa, S. *Angew. Chem., Int. Ed.* 2004, 43, 2684-2687.
5. See, for example: a) Hafizovic, J.; Bjorgen, M.; Olsbye, U.; Dietzel, P. D. C.; Bordiga, S.; Prestipino, C.; Lamberti, C.; Lillerud, K. P. *J. Am. Chem. Soc.* 2007, 129, 3612-3620. b) Ma, S.; Sun, D.; Ambrogio, M.; Fillinger, J. A.; Parkin, S.; Zhou, H.-C. *J. Am. Chem. Soc.,* 2007, 129, 1858-1859.
6. Sudik, A. C.; Millward, A. R.; Ockwig, N. W.; Côté, A. P.; Kim, J.; Yaghi, O. M. *J. Am. Chem. Soc.,* 2005, 127, 7110-7118.
7. Sun, D.; Ma, S.; Ke, Y.; Collins, D. J.; Zhou, H. *J. Am. Chem. Soc.* 2006, 128, 3896-3897.
8. Ma, B., Mulfort; K. L., Hupp; J. T., *Inorgan. Chem.,* 2005, 44, 4912-4914.
9. Eddaoudi, M.; Kim, J.; Rosi, N.; Vodak, D; Wachter, J; OKeefe, M; Yaghi, O. M., *Science,* 2002, 295, 469-72.
10. Yaghi, M. O. et al. U.S. Pat. No. 6,930,193

The invention claimed is:

1. A method of purification of a solid mixture of a metal-organic framework (MOF) material and a second material, comprising disposing the solid mixture containing a MOF material to be isolated and the second material in a first liquid separation medium having a density greater than that of the MOF material and introducing a second liquid separation medium that is miscible in the first liquid separation medium and having a density less than that of the first liquid separation medium in a manner to adjust the collective density of the liquid separation medium so that it lies between those of the MOF material and the second material, whereby the solid mixture separates into a floating fraction of the MOF material and a sinking fraction of the second material.

2. The method of claim 1 including isolating a crystalline MOF material from a mixture containing a second material comprising the same organic-strut and/or metal-ion building blocks.

3. The method of claim 1 including separating of a mixed-organic strut MOF material from a second MOF material containing only a single type of organic strut.

4. The method of claim 1 including separating a non-interpenetrating MOF material from an otherwise identical material consisting of catenated networks.

5. The method of claim 1 including a separating different MOF morphologies.

6. The method of claim 1 including separating a catalytically active MOF material and a non-active species of the MOF material.

* * * * *